(12) United States Patent
Simpson et al.

(10) Patent No.: US 9,119,904 B2
(45) Date of Patent: Sep. 1, 2015

(54) GUIDE WIRE UTILIZING A NICKEL—TITANIUM ALLOY HAVING HIGH ELASTIC MODULUS IN THE MARTENSITIC PHASE

(71) Applicant: Abbott Laboratories, Abbott Park, IL (US)

(72) Inventors: John A. Simpson, Carlsbad, CA (US); John F. Boylan, Murrieta, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 155 days.

(21) Appl. No.: 13/791,851

(22) Filed: Mar. 8, 2013

(65) Prior Publication Data
US 2014/0257247 A1 Sep. 11, 2014

(51) Int. Cl.
| | | |
|---|---|---|
| *A61L 31/02* | (2006.01) | |
| *A61M 25/09* | (2006.01) | |
| *B24B 1/00* | (2006.01) | |
| *B21D 22/02* | (2006.01) | |

(Continued)

(52) U.S. Cl.
CPC ............. *A61L 31/022* (2013.01); *A61L 29/02* (2013.01); *A61L 29/123* (2013.01); *A61L 31/124* (2013.01); *A61M 25/09* (2013.01); *B21D 22/02* (2013.01); *B24B 1/00* (2013.01); *C22C 19/03* (2013.01); *A61L 2400/16* (2013.01); *Y10T 29/49826* (2015.01)

(58) Field of Classification Search
CPC .................. A61M 2025/09141; A61M 25/09; A61M 25/0043
USPC ........................................................ 600/585
See application file for complete search history.

(56) References Cited

U.S. PATENT DOCUMENTS 5,477,864 A * 12/1995 Davidson ....................... 600/585
6,139,510 A * 10/2000 Palermo ......................... 600/585

(Continued)

FOREIGN PATENT DOCUMENTS

| EP | 0873734 | 10/1998 |
|---|---|---|
| WO | WO 95/27092 | 10/1995 |

(Continued)

OTHER PUBLICATIONS

Ke-Bin Low et al., Eutectic Liquid Formation in the NiTi—Nb System: New Joining Method for Nitinol Point, Proceedings of the International Conference on Shape Memory and Superelastic Technologies (2008) pp. 829-836.

(Continued)

*Primary Examiner* — Max Hindenburg
(74) *Attorney, Agent, or Firm* — Workman Nydegger; John Kwok

(57) ABSTRACT

Guide wire devices fabricated from a linear pseudo-elastic Ni—Ti alloy and methods for their manufacture. The Ni—Ti alloy that includes nickel, titanium, and about 3 atomic % (at %) to about 30 at % niobium (Nb). Cold working the Ni—Ti alloy stabilizes the alloy's martensitic phase and yields a linear pseudo-elastic microstructure where reversion to the austenite phase is retarded or altogether blocked. The martensitic phase of cold worked, linear pseudo-elastic Ni—Ti—Nb alloy has an elastic modulus that is considerably higher than the comparable cold worked, linear pseudoelastic binary Ni—Ti alloy. This yields a guide wire device that has better torque response and steerability as compared to cold worked, linear pseudoelastic binary Ni—Ti alloy or superelastic binary Ni—Ti alloy.

12 Claims, 4 Drawing Sheets

(51) Int. Cl.
  *A61L 29/02*   (2006.01)
  *A61L 29/12*   (2006.01)
  *A61L 31/12*   (2006.01)
  *C22C 19/03*   (2006.01)

(56) References Cited

U.S. PATENT DOCUMENTS

| | | | |
|---|---|---|---|
| 6,352,515 B1 * | 3/2002 | Anderson et al. | 600/585 |
| 6,428,634 B1 | 8/2002 | Besselink et al. | |
| 6,682,608 B2 * | 1/2004 | Abrams et al. | 148/402 |
| 7,658,761 B2 | 2/2010 | Yamauchi et al. | |
| 7,938,843 B2 * | 5/2011 | Boylan et al. | 606/200 |
| 8,128,579 B2 * | 3/2012 | Chen et al. | 600/585 |
| 8,211,164 B2 | 7/2012 | Kramer-Brown et al. | |
| 8,500,658 B2 * | 8/2013 | Boyle et al. | 600/585 |
| 2001/0049549 A1 | 12/2001 | Boylan et al. | |
| 2002/0082681 A1 | 6/2002 | Boylan et al. | |
| 2009/0068054 A1 | 3/2009 | Ozawa et al. | |
| 2010/0125329 A1 | 5/2010 | Lin et al. | |
| 2012/0041342 A1 | 2/2012 | Purtzer | |
| 2014/0255246 A1 | 9/2014 | Simpson et al. | |
| 2014/0257451 A1 | 9/2014 | Simpson et al. | |

FOREIGN PATENT DOCUMENTS

| | | |
|---|---|---|
| WO | WO 01/82830 | 11/2001 |
| WO | WO 02/36841 | 5/2002 |
| WO | WO 03/097147 | 11/2003 |
| WO | WO 2004/098458 | 11/2004 |

OTHER PUBLICATIONS

Piao, M. et al; Effects of Nb Addition on the Microstructure of Ti—Ni Alloys, Materials Transactions. JIM, Sendai, JP, vol. 33, No. 4, Jan. 1, 1992, pp. 337-345.

Guanjun, Y. et al; Study on the phase equilibria of the TiNiNb ternary system at 900 degrees C, Journal of Alloys and Compounds 297 (2000) pp. 226-230.

Yang, J.H. et al; Stress-Induced Transformation and Superelasticity in NiTiNb Alloys, Journal De Physique IV, Colloque C8, supplement au Journal de Physique III, vol. 5, Dec. 1995 pp. C8-771 to C8-776.

Gupta, K.P.; Phase Diagrams of Ternary Nickel Alloys, Part 2, Ternary Systems Containing CoNiX, MnNiX, MoNiX, NbNiX, NiTaX, NiTiX, NiVX, pp. 163-176.

Zhao, L.C. et al.; Transformation and Mechanical Behavior of a Ni47Ti44Nb9 Shape Memory Alloy, MRS International Meeting on Adv. Mets., vol. 9, 1989, pp. 171-176.

Prima, S.B. et al.; Investigation Methods and Properties of Powered Materials, Powder Metallugy and Metal Ceramics, vol. 34, Nos. 3,4 1995, pp. 155-160.

Gong, C.W. et al.; Martensitic transformation of Ni50Ti45Ta5 shape memory alloy, Journal of Alloys and Compounds 419, 2006, pp. 61-65.

Ma, J.L. et al,; Microstructure and Transformation Behavior of Ni50Ti50-xTax Alloys, Materials Science Forum vols. 327-328, pp. 179-182, 2000.

Guanjun et al.; Constitutional Phases and Transformation Characteristics of a Ni47Ti44Ta9 Alloy, pp. 239-243.

Nickel Tantalum Titanium Ternary Alloy Phase Diagram (Based on 1991 Gupta K.P., ASM Alloy Phase Diagrams Center, 2007, pp. 1-3.

Lekston, Z. et al.; Phase Transformation in TiNiTa Shape Memory Alloy, Solid State Phenomena vol. 130 2007, pp. 147-150.

Schuessler, T. H.; Welding and Joining of TiNi Shape Memory Alloys: Engineering Aspects and Medical Applications, pp. 25-35.

Gong, C.W. et al.; Phase Transformation and second phases in ternary NiTiTa shape memory alloys, Materials Chemistry and Physics 96 (2006) pp. 183-187.

Cheng, Y. et al.; Surface modification of NiTi alloy with tantalum to improve its biocompatibility and radiopacity, J Mater Sci (2006) 41:pp. 4961-4964.

Simpson et al.; Cast Microstructure of a NiTiNb Shape Memory Alloy, Pract. Met. 23, 1986, pp. 357-361.

U.S. Appl. No. 13/791,860, Feb. 13, 2015, Office Action.

* cited by examiner

GUIDE WIRE UTILIZING A NICKEL—TITANIUM ALLOY HAVING HIGH ELASTIC MODULUS IN THE MARTENSITIC PHASE

BACKGROUND

Guide wires are used to guide a catheter for treatment of intravascular sites such as PTCA (Percutaneous Transluminal Coronary Angioplasty), or in examination such as cardio-angiography. For example, a guide wire used in the PTCA is inserted into the vicinity of a target angiostenosis portion together with a balloon catheter, and is operated to guide the distal end portion of the balloon catheter to the target angiostenosis portion.

A guide wire needs appropriate flexibility, pushability and torque transmission performance for transmitting an operational force from the proximal end portion to the distal end, and kink resistance (resistance against sharp bending). To meet such requirements, superelastic materials such as a Ni—Ti alloy and high strength materials have been used for forming a core member (wire body) of a guide wire.

Near equi-atomic binary nickel-titanium alloys are known to exhibit "pseudo-elastic" behavior when given certain cold working processes or cold working and heat treatment processes following hot working. Pseudo-elasticity can be further divided into two subcategories: "non-linear" pseudo-elasticity and "linear" pseudo-elasticity. "Non-linear" pseudo-elasticity is sometimes used by those in the industry synonymously with "superelasticity."

"Non-linear" pseudo-elastic Ni—Ti alloy exhibits upwards of 8% elastic strain (fully-recoverable deformation) by virtue of a reversible, isothermal stress-induced martensitic transformation. Linear pseudo-elasticity exhibits no such flat plateau. Non-linear pseudo-elasticity is known to occur due to a reversible phase transformation from austenite to martensite, the latter more precisely called "stress-induced martensite" (SIM). At room or body temperature and under minimal stress the material assumes a crystalline microstructure structure known as austenite. As the material is stressed, it remains in the austenitic state until it reaches a threshold of applied stress (a.k.a. the "upper plateau stress"), beyond which the material begins to transform into a different crystal structure known as martensite. Upon removal of the applied stress, the martensite reverts back to the original austenite structure with an accompanying return to essentially zero strain (i.e., the original shape is restored).

A "linear" pseudo-elastic Ni—Ti alloy is processed by cold working the material (e.g., by permanently deforming the material such as by wire-drawing) without subsequent heat treatment (i.e., partial or full annealing). Residual permanent deformation, i.e., "cold work," tends to stabilize the martensitic structure so its reversion back to austenite is retarded or altogether blocked. With increasing levels of permanent deformation, the otherwise austenitic material becomes fully martensitic at room and body temperature, and further permanent deformation serves to progressively raise its yield strength. The complete disappearance of austenite via cold work altogether eliminates the plateau (austenite to martensite transformation) on the stress strain curve, and results in a unique stress strain curve without a classic perfectly linear slope and without an apparent yield point.

While linear pseduoelastic binary NiTi is highly durable with good flexibility and pushability, binary NiTi in the linear pseduoelastic state is nevertheless not an ideal material for a guide wire due to its inherently low stiffness [i.e., secant modulus around 5 Msi (~34 GPa) at 4% elongation versus conventional Young's modulus of approximately 28 Msi (~193 GPa) for 316L austenitic stainless steel], which adversely affects torqueability. For example, the low modulus of the material in the martensitic condition (either linear pseudo-elastic martensite or stress-induced martensite found in superelastic Ni—Ti) relative to an austenitic stainless steel makes it challenging to torque a guide wire made from linear pseudo-elastic Ni—Ti alloy because it has a greater tendency to elastically absorb a significant amount of applied twist as opposed to directly transmitting torque from end to end.

BRIEF SUMMARY

The present disclosure describes guide wire devices and methods for their manufacture. Guide wire devices include an elongated shaft member having at least one cold worked, linear pseudoelastic section that includes a Ni—Ti alloy that includes about 3 atomic % (at %) to about 30 at % niobium (Nb). Cold working the Ni—Ti alloy (e.g., the Ni—Ti—Nb alloy) stabilizes the alloy's martensitic phase and yields a linear pseudo-elastic microstructure where reversion to the austenite phase is retarded or altogether blocked. The linear pseudo-elastic Ni—Ti—Nb alloy has an elastic modulus that is considerably higher than comparable cold worked, linear pseudoelastic binary Ni—Ti alloy and is highly durable, corrosion resistant, and shapeable by a user, which facilitates guiding the guide wire through tortuous anatomy. In addition, cold worked Ni—Ti—Nb alloys that exceed the solubility limit of Nb (e.g., about 4%) are believed to have a dual phase microstructure with martensitic Ni—Ti—Nb and Nb-rich phases, which, according to the rule of mixtures, yield a material having an elastic modulus that is considerably higher than comparable cold worked, linear pseudoelastic binary Ni—Ti alloy. As a result, the cold worked Ni—Ti—Nb alloy has better torque response and steerability as compared to cold worked, linear pseudoelastic binary Ni—Ti alloy or superelastic binary Ni—Ti alloy.

In one embodiment, a guide wire device is described. The guide wire device includes an elongated shaft member having a proximal section and a distal section. At least a portion of the elongated shaft member is fabricated from a cold worked nickel-titanium (Ni—Ti) alloy that includes nickel (Ni), titanium (Ti), and niobium (Nb). In one embodiment Nb is present in the Ni—Ti alloy in an amount ranging from about 3 atomic (at %) to about 30 at %. The cold worked Ni—Ti alloy has a linear pseudo-elastic microstructure imparted by cold work that displays linear pseudoelastic behavior.

The relationship between Nb and Ti contents which serves to maintain the transformation temperature (Ms) within a reasonably consistent range is essentially linear over a range from approx. 5 to 30 at. % Nb. This relationship is not 1:1; it is approximately 0.45:1, which means that Nb probably does not substitute 1:1 for Ti in the NiTi matrix. Rather, it appears to partition almost equally (a 0.5:1 relationship representing exactly equal substitution for Ti and for Ni). That is, as more and more Nb is added (in the range from about 5 to about 30 at % Nb), the necessary reduction in Ti required to maintain a desirable Ms transformation temp is nearly half of the Nb addition (i.e., about 0.45), and the reduction in Ni is also nearly half the Nb addition. As such, it is believed that incremental additions of Nb simply generate more of an Nb-rich second phase rather than altering the composition of the NiTi matrix.

In another embodiment, a method for fabricating a guide wire device is disclosed. The method includes (1) fabricating an elongated shaft member that includes a proximal section and a distal section. In one embodiment, at least a portion of the elongated shaft member includes a nickel-titanium (Ni—Ti—Nb) alloy comprising nickel (Ni), titanium (Ti), and niobium (Nb). The method further includes (2) cold working at least the Ni—Ti—Nb alloy to yield a Ni—Ti—Nb alloy having a linear pseudo-elastic microstructure imparted by cold work that displays a martensitic phase.

In yet another embodiment, a method for fabricating a guide wire device that includes a linear pseudo-elastic alloy may include (1) providing an elongated shaft member that includes a proximal end section and a distal end section. According to the present method, the elongated shaft member includes a Ni—Ti—Nb alloy. The Nb is present in the Ni—Ti—Nb alloy in a range from about 3 atomic % (at %) to about 30 at % and Ni is present in an amount about 3 at % higher than an amount of Ti. The method further includes, (2) cold working at least a portion of the Ni—Ti—Nb alloy member to yield a linear pseudo-elastic microstructure having a martensitic phase with linear pseudo-elastic behavior and without a phase transformation or onset of stress-induced martensite, (3) disposing a helical coil section about at least the distal section of the elongated shaft member, coupling the helical coil section to the elongated shaft member, (4) forming an atraumatic cap section on a distal end of the helical coil section, and (5) applying at least one lubricious material to the guide wire device.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which.

DETAILED DESCRIPTION

I. Introduction

Figure 1:
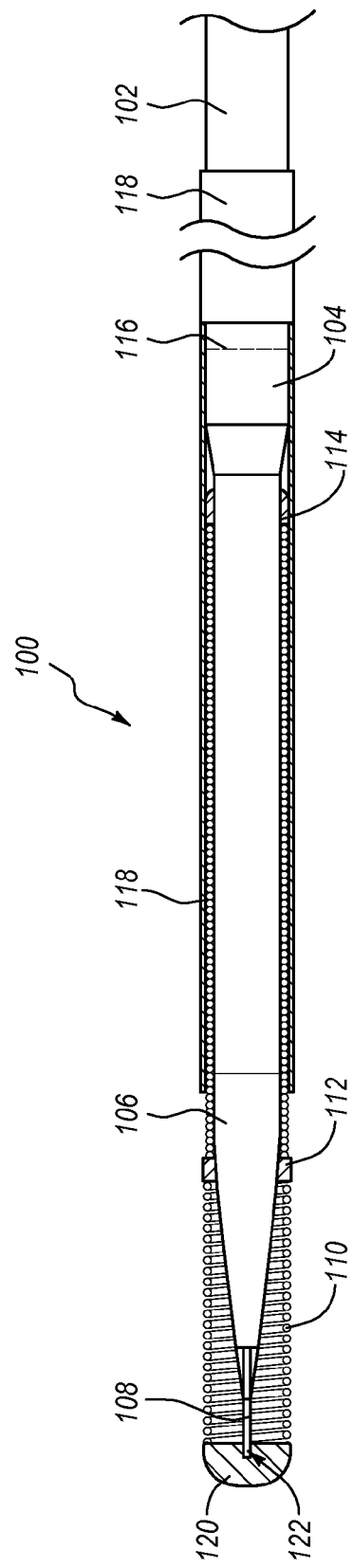
FIG. 1 illustrates a partial cut-away view of a guide wire device according to one embodiment of the present disclosure.

The present disclosure describes guide wire devices and methods for their manufacture. Guide wire devices include an elongated shaft member having at least one cold worked, linear pseudoelastic section that includes a Ni—Ti alloy that includes about 3 atomic % (at %) to about 30 at % niobium (Nb). Cold working the Ni—Ti alloy (e.g., the Ni—Ti—Nb alloy) stabilizes the alloy's martensitic phase and yields a linear pseudo-elastic microstructure where reversion to the austenite phase is retarded or altogether blocked. The linear pseudo-elastic Ni—Ti—Nb alloy is highly durable, corrosion resistant, and shapeable by a user to facilitate guiding the guide wire through tortuous anatomy. In addition, the cold worked Ni—Ti—Nb alloy is known to have a dual phase microstructure with martensitic Ni—Ti and Nb-rich phases, which, according to the rule of mixtures, yields a material having an elastic modulus that is considerably higher than comparable cold worked, linear pseudoelastic binary Ni—Ti alloy. As a result, the cold worked Ni—Ti—Nb alloy has better torque response and steerability as compared to cold worked, linear pseudoelastic binary Ni—Ti alloy or superelastic binary Ni—Ti alloy.

Guide wire devices are used in minimal invasive procedures such as, but not limited to, percutaneous transluminal coronary angioplasty (PTCA) to track through vessels, access and cross lesions, and support interventional devices for a variety of procedures. Guide wire devices have a number of desired performance characteristics such as, but not limited to, flexibility, support, the ability to steer the guide wire device through the patient's vasculature (i.e., trackability), the ability to transmit steering torque from the proximal end of the device outside the patient's body to the distal tip inside (i.e., torqueability), torque control, lubricity, the ability to visualize the guide wire device as it progresses through the patient's body, and tactile feedback. Guide wire design typically involves the balancing of these various characteristics.

In order to, for example, track through a patient's vasculature guide wire devices are quite long and thin. In terms of length, guide wire devices need to be long enough to travel from an access point outside a patient's body to a treatment site and narrow enough to pass freely through the patient's vasculature. Lengths of about 150 cm to about 300 cm are typical. In terms of diameter, typical guide wire device have an overall diameter of about 0.2 mm to about 0.5 mm for coronary use. Larger diameter guide wires may be employed in peripheral arteries and other body lumens. The diameter of the guide wire device affects its flexibility, support, and torque. Thinner wires are more flexible and are able to access narrower vessels while larger diameter wires offer greater support and torque transmission.

II. Guide Wire Devices

In one example embodiment of the present invention, a guide wire device fabricated from a Ni—Ti—Nb alloy is described. The guide wire device includes an elongated shaft member having a proximal section and a distal section. At least a portion of the elongated shaft member is fabricated from a cold worked nickel-titanium (Ni—Ti) alloy that includes nickel (Ni), titanium (Ti), and niobium (Nb). In one embodiment Nb is present in the Ni—Ti alloy in an amount ranging from about 3 atomic % (at %) to about 30 at %. The cold worked Ni—Ti alloy exhibits linear pseudoelastic behavior. In one embodiment, the Ni is present in the Ni—Ti alloy in an amount about 3 at % higher than a corresponding amount of Ti.

The Ni—Ti—Nb alloys discussed herein have a considerably higher elastic modulus (i.e., Young's modulus) in the cold worked, linear pseudo-elastic martensitic phase as compared to binary Ni—Ti in the martensitic phase. As will be discussed in greater detail below, it is believed that the Ni—Ti—Nb alloy has a dual phase microstructure that includes martensitic Ni—Ti and Nb-rich phases. It is believed that the Nb-rich phase, which has a considerably higher Young's modulus than Ni—Ti, interacts with the martensitic Ni—Ti and serves to raise the Young's modulus of the overall structure. As mentioned previously herein, the martensitic phase of binary Ni—Ti is present when the metal is in the cold worked, linear pseudo-elastic state and when the metal in the superelastic state is converted from austenite to martensite by the application of stress (i.e., stress-induced martensite or SIM).

In ordinary applications, differences in elastic modulus between two materials can be readily compensated for by dimensional alterations. That is, for example, the inherent floppiness of a wire material that has a low elastic modulus can ordinarily be compensated for by increasing the diameter of the wire in order to attain equivalent deflection behavior when compared to a wire material with a higher elastic modulus. However, guide wire devices typically face inherent dimensional constraints that are imposed by the overall product profile, by the allowable space within overlying coils or polymeric jacketing, the size of the anatomy to be accessed, or combinations thereof. For this reason, the Ni—Ti—Nb alloys discussed herein, which have higher stiffness in the linear pseudoelastic state than comparable binary Ni—Ti, significantly expand the maximum range of torsional or bending stiffness that can be achieved in a guide wire of a given profile.

Referring now to FIG. 1, a partial cut-away view of an example of a guide wire device 100 that embodies features of the invention is illustrated. The guide wire device 100 may be adapted to be inserted into a patient's body lumen, such as an artery or another blood vessel. The guide wire device 100 includes an elongated proximal portion 102 and a distal portion 104. In one embodiment, both the elongated proximal portion 102 and the distal portion 104 may be formed from a Ni—Ti—Nb alloy. In another embodiment, the elongated proximal portion 102 may be formed from a first material such as stainless steel (e.g., 316L stainless steel) or a Ni—Ti alloy and the distal portion may be formed from a second material such as a Ni—Ti—Nb alloy. In embodiments where the elongated proximal portion 102 and the distal portion 104 are formed from different materials, the elongated proximal portion 102 and the distal portion 104 may coupled to one another via a welded joint 116 that couples the proximal portion 102 and the distal portion 104 into a torque transmitting relationship.

In one embodiment, selected portions of the guide wire device 100 or the entire guide wire device 100 may be cold worked in order to yield a linear pseudo-elastic microstructure. As mentioned elsewhere herein, increasing levels of cold-work (i.e., permanent deformation without subsequent heat treatment) progressively raises the yield strength of the material and leads to almost the complete disappearance of austenite and the elimination of the plateau (austenite to martensite transformation) on the stress strain curve and results in a unique stress strain curve without a classic linear modulus of elasticity and without an apparent yield point.

In one embodiment, selected portions of the guide wire device 100 or the entire guide wire device 100 may be cold worked to impart a linear pseudo-elastic microstructure that includes about 20% to about 90% cold work, about 30% to about 65% cold work, about 40% cold work to about 50% cold work, or about 45% cold work. Depending on the composition of the Ni—Ti—Nb alloy (e.g., about 38 at % to about 47 at % Ni, about 35 at % to about 44 at % Ti, and about 9 at % to about 27 at % Nb) and the amount of cold work, the Ni—Ti—Nb alloy may have an elastic modulus of about 50 gigapascals (GPa) to about 100 GPa or an elastic modulus of about 60 GPa to about 70 GPa.

Referring again to FIG. 1, the distal portion 104 has at least one tapered section 106 that, in the illustrated embodiment, becomes smaller in the distal direction. The length and diameter of the tapered distal core section 106 can, for example, affect the trackability of the guide wire device 100. Typically, gradual or long tapers produce a guide wire device with less support but greater trackability, while abrupt or short tapers produce a guide wire device that provides greater support but also greater tendency to prolapse (i.e., kink) when steering.

In the illustrated embodiment, the tapered distal core section 106 may further include a shapeable distal end section 108. Ni—Ti alloys such as Ni—Ti—Nb are shapeable in the linear pseudoelastic state. The linear pseudoelastic state can be imparted to the Ni—Ti alloy by cold work, with varying amounts of cold work imparting different degrees of linear pseudoelasticity and differing degrees of shapeability. Linear pseudoelastic Ni—Ti alloy can readily be permanently deformed by straining the material beyond its elastic strain limit, which is less than that of superelastic Ni—Ti alloy. As such, the shapeable distal end section 108 can allow a practitioner to shape the distal and of the guide wire device 100 to a desired shape (e.g., a J-bend) for tracking through the patient's vasculature.

In one embodiment, the shapeable distal end section 108 is manufactured by grinding the distal end of the Ni—Ti distal section 104 to a first cross-sectional dimension (e.g., by centerless grinding) and cold-working (e.g., by flattening) the ground portion to a second cross-sectional dimension. For example, the first dimension can be in a range from about 0.1 mm to about 0.07 mm, or about 0.08 mm. The second cross-sectional dimension, which is formed by, for example, cold-work flattening at least a part of the ground distal section, is in a range from about 0.065 mm to about 0.008 mm, about 0.055 mm to about 0.03 mm, about 0.05 to about 0.04 mm, or about 0.045 mm.

The length of the distal end section 106 can, for example, affect the steerability of the guide-wire device 100. In one embodiment, the distal end section 106 is about 10 cm to about 40 cm in length. In another embodiment, the distal end section 106 is about 2 to about 6 cm in length, or about 2 to 4 cm in length.

As illustrated in FIG. 1, the guide wire device 100 includes a helical coil section 110. The helical coil section 110 affects support, trackability, and visibility of the guide wire device and provides tactile feedback. In some embodiments, the most distal section of the helical coil section 110 is made of radiopaque metal, such as platinum or a platinum-nickel or platinum-iridium alloy, to facilitate the observation thereof while it is disposed within a patient's body. As illustrated, the helical coil section 110 is disposed about at least a portion of the distal portion 104 and has a rounded, atraumatic cap section 120 on the distal end thereof. The helical coil section 110 is secured to the distal portion 104 at proximal location 114 and at intermediate location 112 by a suitable technique such as, but not limited to, soldering, brazing, or welding.

In one embodiment, the distal end section 108 may be secured to the rounded, atraumatic cap section 120 by virtue of a joint 122 such as, but not limited to, a soldered, brazed, or welded joint. Because Ni—Ti alloy forms a persistent oxide layer, it can be difficult to solder Ni—Ti. Therefore, in one embodiment, the distal end section 108 may be joined to the atraumatic cap section 120 using a soldering technique specially adapted to soldering Ni—Ti alloys. Briefly stated here, the distal end section 108 is prepared and a layer of solder material is applied thereto and the distal end section 108 is soldered to the rounded, atraumatic cap section 120 to form a soldered joint 122.

In one embodiment, portions of the guide wire device 100 are coated with a coating 118 of lubricous material such as polytetrafluoroethylene (PTFE) (sold under the trademark Teflon by du Pont, de Nemours & Co.) or other suitable lubricous coatings such as the polysiloxane coatings, polyvinylpyrrolidone (PVP), and the like.

Figure 2:
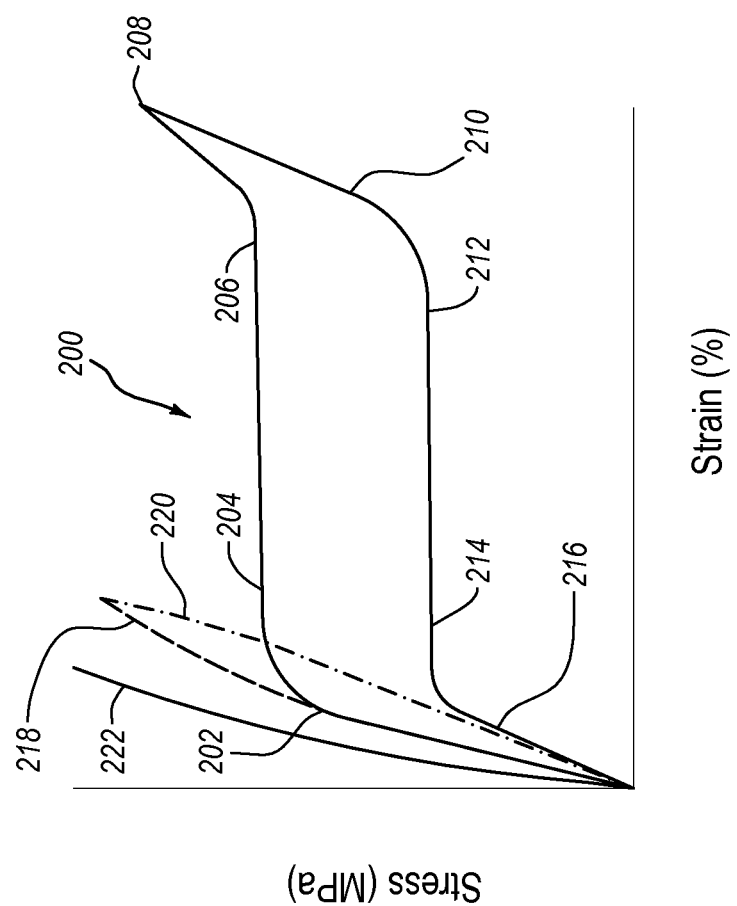
FIG. 2 illustrates stress-strain curves for stainless steel, a linear pseudo-elastic Ni—Ti alloy, and a superelastic (i.e., non-linear pseudo-elastic) NiTi.

To illustrate the foregoing points, FIG. 2 contains the elastic component of three idealized stress-strain curves for 316L stainless steel 222, linear pseudoelastic Ni—Ti—Nb alloy 218 and 220, and non-linear pseudoelastic Ni—Ti alloy 200. The stress/strain relationship is plotted on x-y axes, with the x axis representing strain and the y axis representing stress.

In curve 224, when stress is applied to a specimen of a metal such as Ni—Ti or a Ni—Ti alloy exhibiting non-linear pseudoelastic characteristics at a temperature at or above the temperature at which the transformation of the martensitic phase to the austenitic phase is complete, the specimen deforms elastically 202 until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve 224, this is represented by the upper, nearly flat stress plateau 204 at approximately 70 to 80 ksi. The strain increases while the stress remains essentially constant until the transformation of the austenitic phase to the martensitic phase is complete 206. Thereafter, further increase in stress is necessary to cause further deformation 208. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in stress 210. As stress reduction reaches the level at which the martensitic phase transforms back into the austenitic phase 212, the stress level in the specimen remains essentially constant 214 (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau 214 at about 20 ksi.

After the transformation back to austenite is complete, further stress reduction results in elastic strain reduction 216. This ability to incur significant strain at relatively constant stress upon the application of a load and to recover from the deformation upon the removal of the load is commonly referred to as non-linear pseudoelasticity (or superelasticity).

FIG. 2 also includes a curve 218-220 representing the idealized behavior of linear pseudoelastic Ni—Ti—Nb alloy as utilized in embodiments of the present invention. Curve 218-220 does not contain any flat plateau stresses found in curve 224. This stands to reason since the Ni—Ti—Nb alloy of curve 218-220 remains in the martensitic phase throughout and does not undergo any phase change. Curve 218-220 shows that increasing stress begets a proportional increase in reversible strain, and a release of stress begets a proportional decrease in strain. The areas bounded by curves 224 and 218-220 represent the hysteresis in the Ni—Ti alloy.

As is apparent from comparing curve 218-220 to curve 224 in FIG. 2, with the use of linear pseudoelastic Ni—Ti—Nb alloy, the mechanical strength of the disclosed medical devices is substantially greater per unit strain than a comparable device made of superelastic Ni—Ti alloy. Consequently, a major benefit is that smaller component parts such as the shapeable distal end section 108 can be used because of the greater storage of energy available in a linear pseudoelastic Ni—Ti—Nb alloy device. A small profile is one critical factor for crossing narrow lesions or for accessing remote and tortuous arteries.

FIG. 2 also includes curve 222 which is the elastic behavior of a standard 316L stainless steel. Stress is incrementally applied to the steel and, just prior to the metal deforming plastically, decrementally released.

Figure 3:
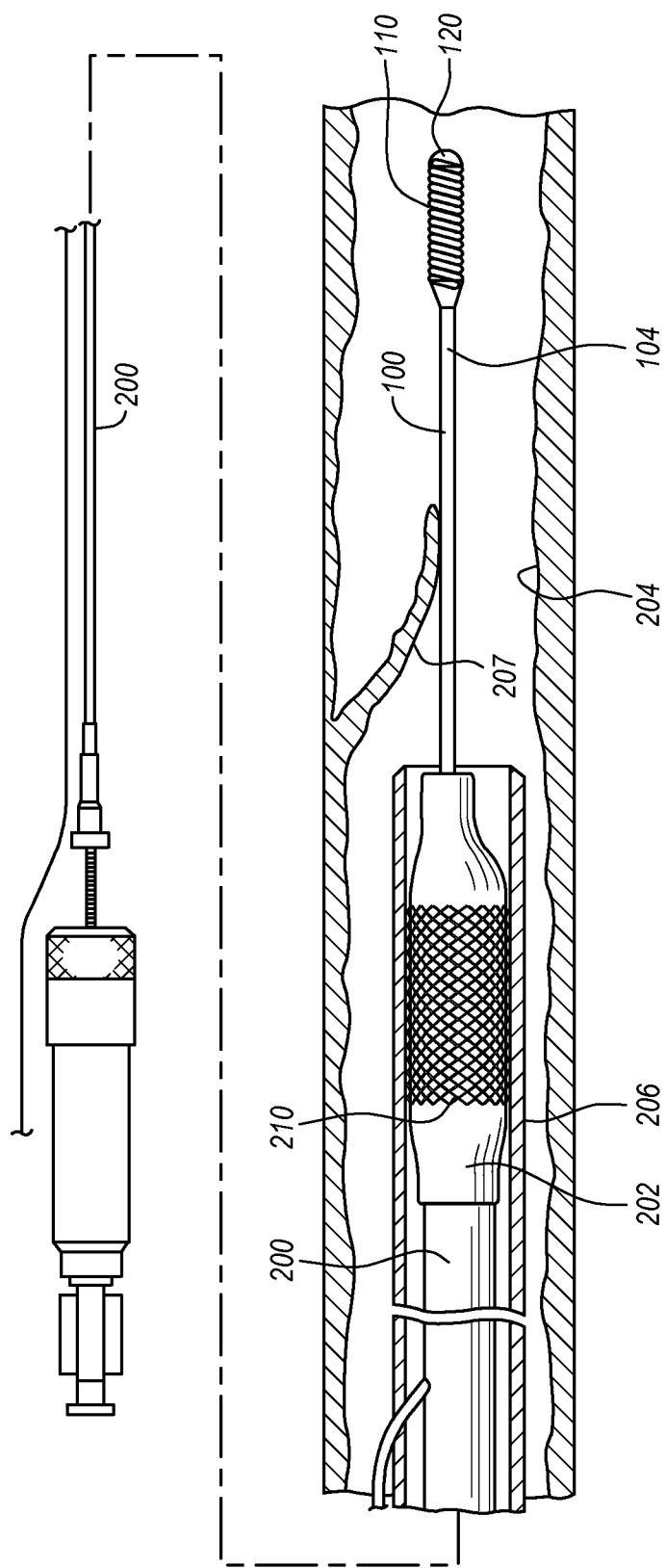
FIG. 3 illustrates a superelastic Ni—Ti—Nb alloy.
Figure 4:
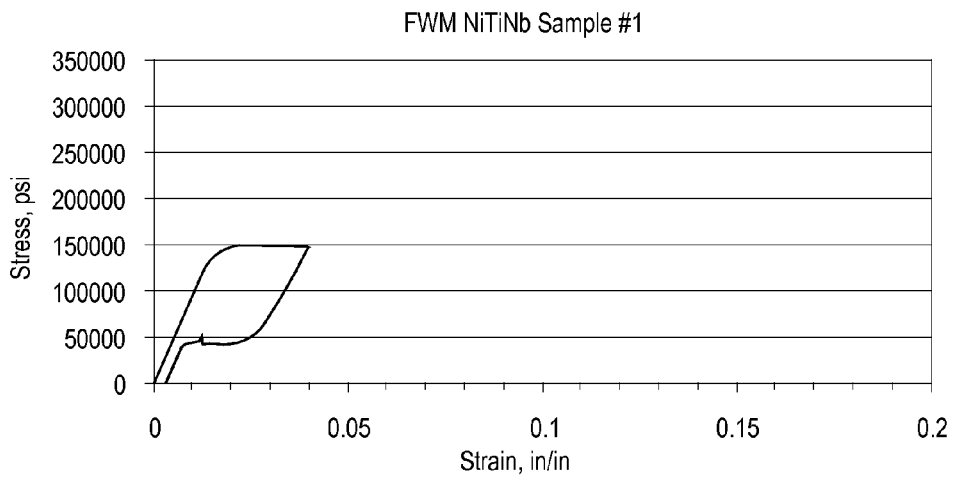
FIG. 4 illustrates a linear pseudoelastic Ni—Ti—Nb alloy.
Figure 5:
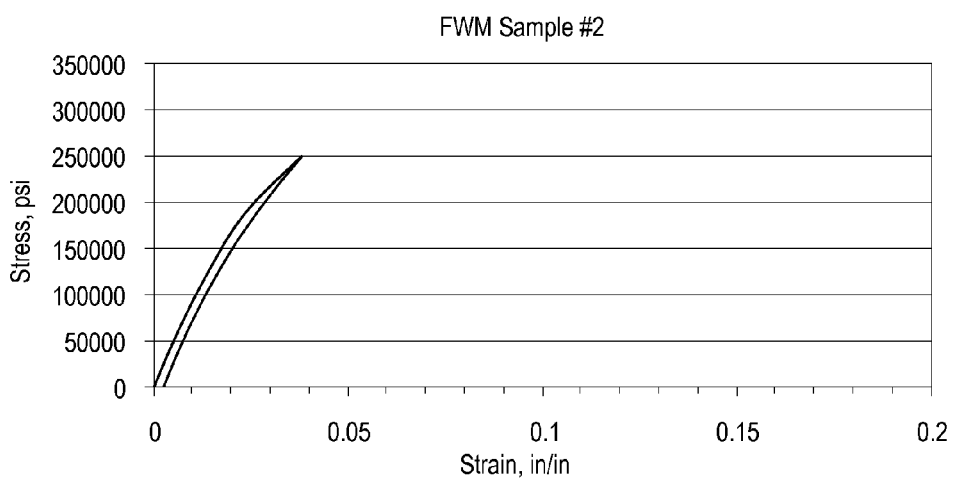
FIG. 5 represents a superelastic Ni—Ti—Nb alloy that has been processed to have a narrow hysteresis loop.

Referring now to FIGS. 3-5, tensile test curves of three versions of a Ni—Ti—Nb alloy (i.e., 44Ti47Ni9Nb) are shown. FIGS. 3-5 represent samples from the same lot of Ni—Ti—Nb alloy that have been processed differently to achieve different properties. FIG. 3 represents a superelastic Ni—Ti—Nb alloy, FIG. 4 represents a linear pseudoelastic Ni—Ti—Nb alloy, and FIG. 5 represents a superelastic Ni—Ti—Nb alloy that has been processed to have a narrow hysteresis loop.

The superelastic Ni—Ti—Nb alloy represented in FIG. 3 has an upper plateau stress at about 147 ksi, a lower plateau stress of about 100 ksi and a stress hysteresis width (i.e., the distance between the upper and lower plateau stresses) of about 47 ksi.

The curve illustrated in FIG. 4 for the linear pseudoelastic Ni—Ti—Nb alloy is similar to the curve 218-220 illustrated in FIG. 2. The curve illustrated in FIG. 4 does not contain any flat plateau stresses and increasing stress begets a proportional increase in reversible strain, and a release of stress begets a proportional decrease in strain. The alloy illustrated in FIG. 4 has a Young's modulus of about 8.8 Msi (i.e., about 60 GPa).

The superelastic Ni—Ti—Nb alloy that has been processed to have a narrow hysteresis loop shown in FIG. 5 has been processed with relatively significant amounts of cold wirk (e.g., about 30 to 50% cold work) followed by limited heat treatment. The Ni—Ti—Nb alloy represented in FIG. 5 has an upper plateau stress at about 180 ksi, a lower plateau stress of about 165 ksi and a stress hysteresis width (i.e., the distance between the upper and lower plateau stresses) of about 15 ksi. Raising the plateau stress and narrowing the stress hysteresis width of Ni—Ti—Nb relative to conventionally processed Ni—Ti—Nb can significantly improve the steerability of a guide wire device while maintaining the flexibility, durability, and kink resistance that is typical of superelastic Ni—Ti—Nb alloys.

Figure 6:
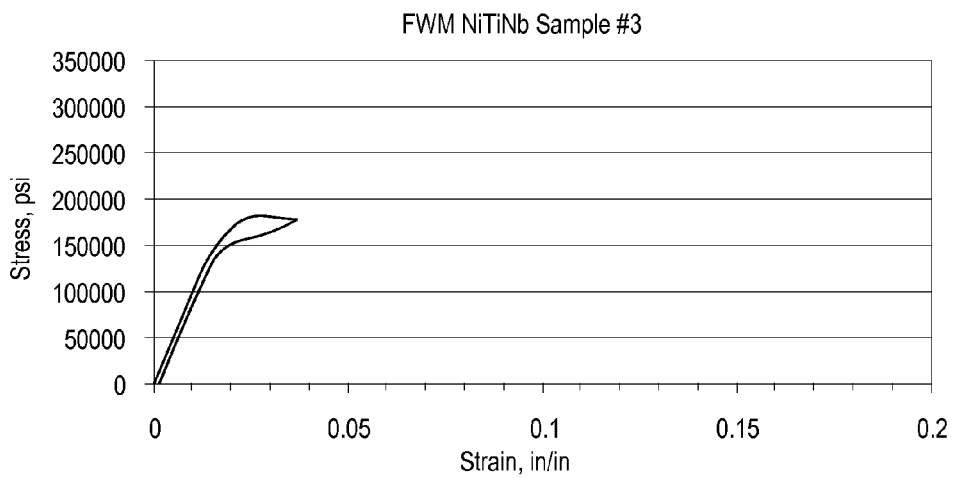
FIG. 6 is a side elevation view, in partial cross-section, of a delivery catheter within a body lumen having a stent disposed about the delivery catheter according to an embodiment of the present disclosure.

Referring now to FIG. 6, the guide wire device 100 is shown configured to facilitate deploying a stent 210. FIG. 6 provides more detail about the manner in which the guide wire device 100 may be used to track through a patient's vasculature where it can be used to facilitate deployment of a treatment device such as, but not limited to the stent 210. FIG. 6 illustrates a side elevation view, in partial cross-section, a delivery catheter 200 having a stent 210 disposed thereabout according to an embodiment of the present disclosure. The portion of the illustrated guide wire device 100 that can be seen in FIG. 6 includes the distal portion 104, the helical coil section 110, and the atraumatic cap section 120. The delivery catheter 200 has an expandable member or balloon 202 for expanding the stent 210, on which the stent 210 is mounted, within a body lumen 204 such as an artery.

The delivery catheter 200 may be a conventional balloon dilatation catheter commonly used for angioplasty procedures. The balloon 202 may be formed of, for example, polyethylene, polyethylene terephthalate, polyvinylchloride, nylon, Pebax™ or another suitable polymeric material. To facilitate the stent 210 remaining in place on the balloon 202 during delivery to the site of the damage within the body lumen 204, the stent 210 may be compressed onto the balloon 202. Other techniques for securing the stent 210 onto the balloon 202 may also be used, such as providing collars or ridges on edges of a working portion (i.e., a cylindrical portion) of the balloon 202.

In use, the stent 210 may be mounted onto the inflatable balloon 202 on the distal extremity of the delivery catheter 200. The balloon 202 may be slightly inflated to secure the stent 210 onto an exterior of the balloon 202. The catheter/stent assembly may be introduced within a living subject using a conventional Seldinger technique through a guiding catheter 206. The guide wire 100 may be disposed across the damaged arterial section with the detached or dissected lining 207 and then the catheter/stent assembly may be advanced over the guide wire 100 within the body lumen 204 until the stent 210 is directly under the detached lining 207. The balloon 202 of the catheter 200 may be expanded, expanding the stent 210 against the interior surface defining the body lumen 204 by, for example, permanent plastic deformation of the stent 210. When deployed, the stent 210 holds open the body lumen 204 after the catheter 200 and the balloon 202 are withdrawn.

III. Ni—Ti—Nb Alloys

Embodiments of the present invention provide guide wire devices 100 that include Ni—Ti alloys which, in the martensitic phase, possess substantially greater elastic modulus and shear modulus than binary nitinol in the martensitic phase. Alloys having linear pseudoelastic characteristics and a high elastic modulus and shear modulus facilitate torque transmission, steerability, and shapeability of guide wire devices to facilitate the advancing of the guide wire in a body lumen. The linear pseudoelastic Ni—Ti alloys exhibit extensive, recoverable strain, which greatly minimizes the risk of performance loss due to kinking with possible concomitant damage to arteries during the advancement therein.

One such example of Ni—Ti alloys is the family of alloys containing nickel (Ni), titanium (Ti), and niobium (Nb). In one embodiment, Nb is present in the Ni—Ti alloy in an amount ranging from about 3 atomic % (at %) to about 30 at %, and Ni is present in an amount about 3 at % higher than an amount of Ti.

At some component ratios, the Ni—Ti—Nb alloy may form a dual phase microstructure. The preferred dual phase microstructure consists of Ni—Ti with about 3 at % Nb in solution and a dispersed second phase, consisting largely of niobium, which naturally arises by virtue of a eutectic reaction during solidification. And while the primary phase and the dispersed phase may include the same components, the niobium content will generally be much higher in the dispersed phase as compared to the primary phase. Further, the niobium-rich second phase is known to be ductile and is coherent with the primary Ni—Ti phase.

In some cases, the dual phase microstructure exhibits qualities of a so-called metal matrix composite. The term metal matrix composite (MMC) encompasses a wide range of scales and microstructures; however, the bulk properties of an MMC are typically accounted for by the so-called "rule of mixtures," which describes the properties of a composite in terms of a volume weighted average of the properties of each of the individual phases (i.e., the primary and dispersed phases). While the rule of mixtures is to some extent an approximation, it does provide a useful metric for understanding the properties of the Ni—Ti—Nb alloy system.

The Ni—Ti—Nb alloy system includes two ductile phases having widely different mechanical properties. Cast ingots of the Ni—Ti—Nb alloy would contain a structure consisting of the primary dendrites of a first phase (i.e., either Ni—Ti or Ni—Ti—Nb) and a eutectic mixture containing the first phase and a second phase (i.e., the niobium-rich phase). Upon working down the cast material to produce a guide wire structure (e.g., by one or more of drawing, stamping, rolling, flattening, swaging, or other suitable working techniques), the cast structure would become elongated in the direction of working.

The niobium-rich phase (body centered cubic or "bcc" Nb) coexists with the Ni—Ti phase in some alloys, provided the alloy contains sufficient Nb. Where the linear pseudo-elastic martensite structure is induced within the Ni—Ti-rich phase by cold working, the observed properties of the bulk material are a blend of what would be predicted from a mixture of linear pseudo-elastic Ni—Ti and nearly pure niobium having a bcc crystalline structure. For further discussion of Ni—Ti—Nb alloy systems see, e.g., Eutectic Liquid Formation in the NiTi—Nb System: New Joining Method for Nitinol Point, Ke-Bin Low et al., Proceedings of the International Conference on Shape Memory and Superelastic Technoligies (2008) pp. 829-836.

Nonetheless, it is worth mentioning that the compositions specifically discussed herein (e.g., 47 at % Ni, 44 at % Ti and 9 at % Nb) do not appear in the Ke-Bin Low reference incorporated above. This is because, due to relative similarities in outer shell valence and atomic radii, Nb appears to be capable of substituting freely for up to about 2 at % to 4 at % or about 3 at % Ti in the Ni—Ti-rich phase but not for Ni (Note: if Nb were to substitute equally for Ti and Ni, then the resulting composition would be 45.5 at % Ni, 45.5 at % Ti and 9 at % Nb, which can be found in Ke-Bin Low). Given that the example composition (i.e., 47 at % Ni, 44 at % Ti and 9 at % Nb) contains about 3 at % less Ti than Ni, it is anticipated that the Ni—Ti-rich phase contains about 3 at % Nb, leaving an excess of about 6 at % Nb that exists as the Nb-rich phase identified in FIG. 7 of the Ke-Bin Low reference as "bcc-Nb." Given this approximation where the solubility of Nb in the Ni—Ti-rich phase appears to be somewhere in the range of about 2 at % to 4 at %, one will appreciate that increasing the amount of niobium will increase the volume fraction of the Nb-rich, dispersed phase without affecting the composition of the Ni—Ti-rich phase.

Therefore, if one were attempting to formulate new Ni—Ti—Nb alloys, a first approximation would be to constrain the Ni and Ti compositions such that the amount of Ni always exceeds the amount of Ti by an amount somewhere in the range of about 2 at % to 4 at % (e.g., about 3 at %). Following this rule, suitable examples of Ni—Ti—Nb alloys may include about 36.5 at % to about 50 at % Ni, about 33.5 at % to about 47 at % Ti, and about 3 at % to about 30 at % Nb. In a number of specific examples within the ranges recited herein, the Ni—Ti alloy may include about 50 at % Ni, about 47 at % Ti, and about 3 at % Nb; about 48.5 at % Ni, about 45.5 at % Ti, and about 6 at % Nb; about 47 at % Ni, about 44 at % Ti, and about 9 at % Nb; about 42.5 at % Ni, 39.5 at % Ti, and about 18 at % Nb; about 38 at % Ni, about 35 at % Ti, and about 27 at % Nb; about 36.5 at % Ni, about 33.5 at % Ti, and about 30 at % Nb. Some adjustment in the ratio of Ni to Ti may be preferred to fine tune the transformation temperature of the Ni—Ti-rich phase and thus its ability to be processed into the desired linear elastic martensite structure.

IV. Methods for Fabricating a Guide Wire Device

In one embodiment, a method for fabricating a guide wire device is disclosed. The method includes (1) fabricating an elongated shaft member that includes a proximal section and a distal section. In one embodiment, at least a portion of the elongated shaft member includes a nickel-titanium (Ni—Ti) alloy that includes nickel (Ni), titanium (Ti), and niobium (Nb). The method further includes (2) cold working at least the Ni—Ti alloy to yield a Ni—Ti alloy that exhibits linear pseudo-elastic behavior in the martensitic phase.

In another embodiment, a method for fabricating a guide wire device that includes a linear pseudo-elastic alloy includes (1) providing an elongated shaft member that includes a proximal end section and a distal end section. According to the present method, the elongated shaft member includes a Ni—Ti—Nb alloy. The Nb is present in the Ni—Ti—Nb alloy in a range from about 3 at % to about 30 at % and Ni is present in an amount about 3 at % higher than an amount of Ti. The method further includes, (2) cold working at least a portion of the Ni—Ti—Nb alloy member to impart a martensitic phase with linear pseudo-elastic behavior and without a phase transformation or onset of stress-induced martensite, (3) disposing a helical coil section about at least the distal section of the elongated shaft member, coupling the helical coil section to the elongated shaft member, (4) forming an atraumatic cap section on a distal end of the helical coil section, and (5) applying at least one lubricious material to the guide wire device.

In one embodiment, the elongated shaft member can be fabricated from a billet or ingot of the Ni—Ti—Nb alloy using at least one of drawing or grinding. Suitable examples of cold working procedures that can be used to cold work either selected sections of the elongated shaft member or the whole elongated shaft member include, but are not limited to, drawing, high force flattening, stamping, rolling, calendaring, and combinations thereof.

In one embodiment, the cold-worked section(s) may include about 20% to about 90% cold work, about 30% to about 65% cold work, about 40% cold work to about 50% cold work, or about 45% cold work. The cold work imparts a martensitic phase having a linear pseudo-elastic microstructure with linear pseudo-elastic behavior without a phase transformation or onset of stress-induced martensite. In one embodiment, the martensitic phase is enhanced and/or stabilized by the cold working. Depending on the composition of the Ni—Ti—Nb alloy and the amount of cold work, the Ni—Ti—Nb alloy may have an elastic modulus of about 50 gigapascals (GPa) to about 100 GPa or an elastic modulus of about 60 GPa to about 70 GPa.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guide wire device, comprising:
   an elongated shaft member having a proximal section and a distal section;
   at least a portion of the elongated shaft member being fabricated from a cold worked nickel-titanium (Ni—Ti) alloy comprising nickel (Ni), titanium (Ti), and niobium (Nb),
      wherein Ni is present in the Ni—Ti alloy in an amount ranging from about 36.5 atomic % (at %) to about 50 at %, Ti is present in the Ni—Ti alloy in an amount ranging from about 33.5 at % to about 47 at %, Nb is present in the Ni—Ti alloy in an amount ranging from about 3 at % to about 30 at %, and Ni is present in the Ni—Ti alloy in an amount about 2 at % to 4 at % higher than the amount of Ti, and
      wherein the cold worked Ni—Ti alloy exhibits linear pseudoelastic behavior.

2. The guide wire device of claim 1, wherein Ni is present in the Ni—Ti alloy in an amount about 3 at % higher than the amount of Ti.

3. The guide wire device of claim 2, wherein the Ni—Ti alloy comprises about 38 at % to about 47 at % Ni, about 35 at % to about 44 at % Ti, and about 9 at % to about 27 at % Nb.

4. The guide wire device of claim 2, wherein the Ni—Ti alloy comprises about 47 at % Ni, about 44 at % Ti, and about 9 at % Nb.

5. The guide wire device of claim 1, further comprising:
   a helical coil section disposed about at least the distal section, wherein the helical coil section is coupled to the elongated shaft member; and
   an atraumatic cap section coupled to a distal end of the helical coil section.

6. The guide wire device of claim 1, wherein the elongated shaft member further comprises at least one of a stainless steel portion or a superelastic nickel-titanium alloy portion.

7. The guide wire device of claim 1, wherein the linear pseudo-elastic microstructure includes about 20% to about 50% cold work.

8. The guide wire device of claim 1, wherein linear pseudo-elastic microstructure includes about 40% to about 50% cold work.

9. The guide wire device of claim 1, wherein at least a portion of the linear pseudo-elastic microstructure is in a martensitic phase.

10. The guide wire device of claim 9, wherein the cold worked Ni—Ti alloy has an elastic modulus of about 50 gigapascals (GPa) to about 100 GPa.

11. The guide wire device of claim 9, wherein the cold worked Ni—Ti alloy has an elastic modulus of about 60 GPa to about 70 GPa.

12. The guide wire device of claim 9, wherein the martensitic phase exhibits linear pseudo-elastic behavior without a phase transformation or onset of stress-induced martensite.

\* \* \* \* \*